| United States Patent [19] | [11] Patent Number: 4,743,596 |
Lapin | [45] Date of Patent: May 10, 1988 |

[54] ANTI-ARTHRITIC PREPARATION

[76] Inventor: Alfred R. Lapin, 6805 Old Alex Ferry Rd., Clinton, Md. 20735

[21] Appl. No.: 62,626

[22] Filed: Jun. 16, 1987

[51] Int. Cl.$^4$ .................. A61K 31/56; A61K 31/62; A61K 31/415
[52] U.S. Cl. .................. 514/161; 514/177; 514/407
[58] Field of Search .................. 514/161

[56] References Cited

U.S. PATENT DOCUMENTS 4,198,402 4/1980 Ezer et al. .................. 514/161
4,232,012 11/1980 Orr et al. .................. 514/161

Primary Examiner—Stanley J. Friedman

[57] ABSTRACT

An anti-arthritic preparation consisting essentially of the anti-inflammatory, nonsteroidal agents aspirin and phenylbutazone, the anti-inflammatory corticosteroid prednisone, and the skeletal muscle relaxant methocarbamol. The use of calcium carbonate and vitamin D as adjuncts is contemplated in protecting against osteoporosis and possible replacement of bone tissue.

6 Claims, No Drawings

ANTI-ARTHRITIC PREPARATION

BRIEF SUMMARY OF THE INVENTION

This invention relates to a new and useful anti-arthritic preparation, and particularly, to an anti-arthritic preparation comprising a combination of anti-inflammatory agents, both nonsteroidal and steroidal, and a skeletal muscle relaxant. More particularly, the invention comprises an anti-arthritic preparation consisting essentially of the anti-inflammatory, nonsteroidal agents aspirin and phenylbutazone, the anti-inflammatory corticosteroid, prednisone, and the skeletal muscle relaxant methocarbamol.

DETAILED DESCRIPTION OF THE INVENTION

The term "arthritis" relates generally to a class of disorders characterized by inflammation of joints, significant members of this class being rheumatoid arthritis and osteoarthritis. Rheumatoid arthritis (RA) is a chronic syndrome characterized by nonspecific, usually symmetric inflammation of the peripheral joints, potentially resulting in progressive destruction of articular and periarticular structures. Osteoarthritis (OA) is the most common form of arthritis and is characterized by degenerative loss of articular cartilage, subchondral bony sclerosis, cartilege and bone proliferation at the joint margins with subsequent osteophyte formation and, commonly, secondary synovial inflammation.

Drug therapy in the treatment of arthritic disorders generally calls for the use of anti-inflammatory agents.

Salicylates, such as aspirin are relatively safe, inexpensive, analgesic, antipyretic and anti-inflammatory. In the case of RA, from 3 to 9 g. (about 10 to 30 five-grain tablets) of aspirin/day are suggested by Merck ("The Merck Manual of Diagnosis and Therapy," 13th Edition, published by Merck Sharp and Dohme Research Laboratories, Division of Merck and Co., Inc., Rahway, N.J. (1977)). The average dose suggested is 4.5 g. (14 tablets) per day, 3 tablets to be given with each of three meals and 5 tablets to be given at bedtime. In the case of OA, about 640 to 960 mg. orally q.i.d. is preferred by Merck. Salicylates such as choline salicylate are recognized as providing better gastrointestinal tolerance than aspirin but less effectiveness as an anti-inflammatory agent.

Water-soluble gold compounds, e.g., gold sodium thiomalate or thiosulfate, are usually given in addition to salicylates if aspirin does not provide sufficient relief in RA. Merck indicates that gold is effective only against active joint inflammation and is not usually helpful in advanced rheumatoid arthritis. Toxic reactions due to sensitivity to the compound may develop, in which case Merck says gold therapy should be stopped immediately and corticosteroid and chelation therapy begun. With regard to corticosteroid therapy Merck suggests topical steroid or oral prednisone 15 to 20 mg/day in divided doses for mild gold dermatitis and larger doses for hematogic complications.

Phenylbutazone is recognized as an anti-inflammatory agent by Merck and by Sloboda (U.S. Pat. No. 4,390,545 issued Jun. 28, 1983) but is indicated by Merck as "rarely effective in RA". Sloboda teaches that a true additive anti-inflammatory effect may be obtained if non-steroidal anti-inflammatory agents, such as aspirin or phenylbutazone, are combined with certain anti-arthritic (and also anti-inflammatory) agents and their tautomeric forms. Merck does indicate that even where phenylbutazone is used in RA, such use must be limited to a short course of 100 mg. q.i.d. orally for 5 to 7 days because of its severe toxic effects. Merck indicates that phenylbutazone may be given in acute symptomatic cases of OA and suggests an initial dose of 100 mg. q.i.d. which is gradually reduced and finally discontinued.

Corticosteroids are recognized by Merck as dramatically effective short-term anti-inflammatory drugs. However, Merck is quick to point out that RA is usually active for many years and clinical benefits from steroids generally diminish with time. Merck points up the fact of complications occurring with long term use in RA and teaches that dosage should not exceed 7.5 mg. of prednisone/day except for severe systemic manifestations. In the case of OA, Merck states "Systemic corticosteroids are contra indicated," but suggests that intra-articular corticosteroids may produce relief, injections being best limited to treatment of acute inflammatory flares precipitated by trauma or joint overuse and that muscle relaxants, for example, diazepam 2 to 5 mg. t.i.d., may be helpful.

It is thus seen that the prior art teaches that non-steroidal and steroidal anti-inflammatory agents may be useful in the treatment of arthritis. While the art specifically identifies a number of non-steroidal anti-inflammatory agents, such as aspirin and phenylbutazone, there is no teaching to combine same. Sloboda, for example, discloses a large number of combinations of non-steroidal agents which give enhanced anti-inflammatory activity, but in all cases the examples are of a single non-steroidal anti-inflammatory agent in combination with a certain anti-arthritic agent containing a nitrile radical.

The prior art also teaches the clinical benefits of corticosteroids in general and prednisone in particular, but makes no suggestion to combine corticosteroids with each other or with non-steroidal anti-inflammatory agents. While there is a suggestion that the use of a muscle relaxant may be helpful, it is limited to OA where corticosteroids are administered intra-articularly.

It has now been discovered that the combination of aspirin with a different non-steroidal anti-inflammatory agent, a steroidal anti-inflammatory agent and a skeletal muscle relaxant unexpectedly proves medically efficacious in the long term systemic treatment of arthritis.

A preferred embodiment of the inventive combination comprises aspirin in combination with the non-steroidal anti-inflammatory agent, phenylbutazone, the corticosteroidal anti-inflammatory agent, prednisone, and the skeletal muscle relaxant, methocarbamol.

Aspirin may be referenced by the chemical name 2-acetyloxy) benzoic acid or acetylsalicylic acid. Its structural formula is

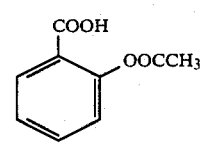

Phenylbutazone may be referenced by the chemical name 4-butyl-1,2-diphenyl-3,5-pyrazolidinedione or 4-butyl-1,2-diphenyl-3,5-dioxopyrazolidine. Its structural formula is

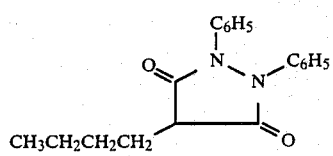

Prednisone may be referenced by the chemical name 17,21-dihydroxypregna-1,4-diene-3,11,20-trione or 1,4-pregnadiene-17,21-diol-3,11,20-trione. Its structural formula is

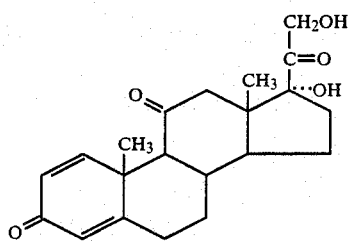

Methocarbamol may be referenced by the chemical name 3-(o-methoxyphenoxy)-1,2-propanediol 1-carbamate or 3-(o-methoxyphenoxy)-2-hydroxypropyl 1-carbamate. Its structural formula is

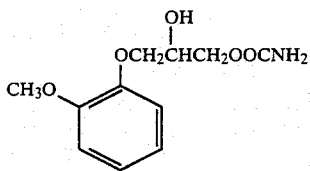

It has been found that in its broadest sense, the synergistic benefits of the inventive preparation may be obtained with aspirin in the range of 81 to 960 mg., phenylbutazone in the range of 50 to 150 mg., prednisone in the range of 1 to 50 mg. and methocarbamol in the range of 500 to 1000 mg.

A specific embodiment of the invention comprises a preparation consisting essentially of aspirin 5 grains, phenylbutazone 100 mg., prednisone 2.5 mg. and methocarbamol 750 mg.

Another specific embodiment of the invention comprises a preparation consisting essentially of aspirin 7.5 grains, phenylbutazone 100 mg. prednisone 5 mg and methocarbamol 750 mg.

It is noted that notwithstanding the employment of but a relatively small amount of the corticosteroid ingredient in the inventive preparation, the steroid presense appears absolutely essential in effecting the synergism necessary to bring about the observed reduction of the inflammatory conditions of the arthritis patients treated. Unless the patient has a history of active ulcer (gastric) or tuberculosis, this ingredient has been an important part of asthma and allergy treatment in children as well as adults, and, in the prescribed dose, appears to have no harmful effect unless specific contraindications are present. An article in the Feb. 25, 1987 issue fo MEDICAL TRIBUNE points out that cortisone derivatives are beneficial (for liver disease) to the degree that their osteoporotic effect is minimal ("2% above the natural bone loss seen in the placebo group"). Accordingly; the embodiments of the inventive preparation contemplate offsetting this possible negative effect by the use of calcium carbonate and vitamin D as adjuncts. In this regard, the invention includes the use of calcium carbonate, preferably about 500 mg., and vitamin D, preferably about 400 I.U., as adjuncts in protecting against osteoporosis and possible replacement of bone tissue.

The anti-arthritic efficacy of the inventive preparation has been demonstrated by clinical application involving 61 test patients exhibiting advanced RA or OA. The classification of these patients by sex and race is as follows:

| Sex | Race | No. of Patients |
| --- | --- | --- |
| Female | White | 27 |
| Female | Black | 11 |
| Male | White | 13 |
| Male | Black | 10 |

The test patients are further classified below by age:

| Age Range | No. of Patients |
| --- | --- |
| Below 40 | 4 |
| 40-49 | 4 |
| 50-59 | 9 |
| 60-69 | 28 |
| Above 69 | 16 |

Treatment of the test patients comprised clinical application of preparations consisting essentially of aspirin 81 to 960 mg., phenylbutazone 50 to 150 mg., prednisone 1 to 50 mg and methocarbamol 500 to 1000 mg. In most cases the preparation consisted essentially of aspirin 5 or 7.5 grains, phenylbutazone 100 mg., prednisone 2.5 or 5 mg., methocarbamol 750 mg., calcium carbonate 500 mg. and vitamin D 400 I.U. Dosage varied from once to three times a day depending upon the degree of inflammation and discomfort. Many patients were able to reduce the dosage periodically, but had to re-establish a larger or regular regimen on occasions, the main circumstances for dosage changes appearing to be (a) change in weather (primarily increased dampness and cold) and (b) amount of exercise. Increased exercise, in some instances, proved beneficial, while in others, exacerbated the discomfort.

Patients were seen usually once a month. They were advised to have a blood count at least every two or three months to assure there were no changes such as may result from antiarthritic medications which might suppress bone marrow activity.

Physical examinations almost inevitably revealed the obvious bone changes: Heberdens' nodes in the finger joint enlargements and the limited motion of larger joints. In questionable cases, X-Rays showed the degenerative processes in the bones and joints associated with osteoarthritis.

In cases involving rheumatoid arthritis, which has more of an infectious or blood involvement basis, joint swelling similar to that of OA was often exhibited.

No significant deleterious hematologic or organic effects were noted in patients under this therapy for three years.

Nine additional patients having allergies or other sensitivities to one or more ingredients of the inventive preparation were excluded from the conclusions. It was significant that, when the allergic causative was determined and removed from the treatment schedule, the patient complained of significant reduction in benefit.

In some cases the allergen was one item, in some cases more than one. The aspirin was present in all the allergic cases and the other allergic substances varied in more than 30% of the other.

An invention has been described that constitutes an advance in the art of anti-arthritic preparations, and, although the preferred embodiments have been described in detail, it should be noted that such details may be altered in a manner within the skill of the art, as, for example, the addition of binders, excipients, disintegrating agents, lubricants, sweetening agents, flavoring agents, time release coatings and the like, as well as the modification of the physical form of the dosage unit, for example, tablets, powders, pills, capsules, and the like, without departing from the scope of the invention as defined in the claims.

I claim:

1. An anti-arthritic preparation consisting essentially of aspirin in the range of 81 to 960 mg., phenylbutazone in the range of 50 to 150 mg., prednisone in the range of 1 to 50 mg., and methocarbamol in the range of 500 to 1000 mg.

2. An anti-arthritic preparation according to claim 1 wherein the aspirin amount is about 5 grains, the phenylbutazone amount is about 100 mg., the prednisone amount is about 2.5 mg. and the methocarbamol amount is about 750 mg.

3. An anti-arthritic preparation according to claim 1 wherein the aspirin amount is about 7.5 grains, the phenylbutazone amount is about 100 mg., the prednisone amount is about 5 mg. and the methocarbamol amount is about 750 mg.

4. An anti-arthritic preparation according to claim in combination with calcium carbonate in the range of 100 to 1000 mg. and vitamin D in the range of 80 to 800 I.U.

5. An anti-arthritic preparation according to claim 4 wherein the aspirin amount is about 5 grains, the phenylbutazone amount is about 100 mg., the prednisone amount is about 2.5 mg., the methocarbamol amount is about 750 mg., the calcium carbonate amount is about 500 mg. and the vitamin D amount is about 400 I.U.

6. An anti-arthritic preparation according to claim 4 wherein the aspirin amount is about 7.5 grains, the phenylbutazone amount is about 100 mg., the prednisone amount is about 5 mg., the methocarbamol amount is about 750 mg., the calcium carbonate amount is about 500 mg. and the vitamin D amount is about 400 I.U.

* * * * *